(12) United States Patent
Rehkemper

(10) Patent No.: US 7,140,373 B2
(45) Date of Patent: Nov. 28, 2006

(54) ELECTRIC ORAL CLEANING DEVICE

(75) Inventor: Steven Rehkemper, Chicago, IL (US)

(73) Assignee: Rehco, LLC, Chicago, IL (US)

( * ) Notice: Subject to any disclaimer, the term of this patent is extended or adjusted under 35 U.S.C. 154(b) by 0 days.

(21) Appl. No.: 10/987,339

(22) Filed: Nov. 12, 2004

(65) Prior Publication Data

US 2005/0284501 A1 Dec. 29, 2005

Related U.S. Application Data

(63) Continuation-in-part of application No. 10/886,235, filed on Jul. 7, 2004.

(60) Provisional application No. 60/582,777, filed on Jun. 25, 2004.

(51) Int. Cl.
*A61C 15/00* (2006.01)

(52) U.S. Cl. .................................... 132/322

(58) Field of Classification Search ........ 132/322–324; 15/167.1, 22.1, 25; 433/118, 143
See application file for complete search history.

(56) References Cited

U.S. PATENT DOCUMENTS

| | | | | |
|---|---|---|---|---|
| 3,927,686 A | * | 12/1975 | Zambito | 132/323 |
| 4,235,253 A | * | 11/1980 | Moore | 132/322 |
| 4,265,257 A | * | 5/1981 | Salyer | 132/322 |
| 4,880,382 A | * | 11/1989 | Moret et al. | 433/118 |
| 5,033,150 A | * | 7/1991 | Gross et al. | 15/22.1 |
| 5,170,809 A | * | 12/1992 | Imai et al. | 132/322 |
| 5,261,430 A | * | 11/1993 | Mochel | 132/322 |
| 5,267,579 A | * | 12/1993 | Bushberger | 132/322 |
| 5,279,314 A | * | 1/1994 | Poulos et al. | 132/322 |
| 5,343,883 A | * | 9/1994 | Murayama | 132/322 |
| 5,411,041 A | * | 5/1995 | Ritter | 132/322 |
| 5,483,982 A | * | 1/1996 | Bennett et al. | 132/323 |
| 5,538,023 A | * | 7/1996 | Oczkowski et al. | 132/323 |
| 5,921,254 A | * | 7/1999 | Carlucci et al. | 132/322 |
| 5,944,033 A | * | 8/1999 | Robinson | 132/322 |
| RE36,699 E | * | 5/2000 | Murayama | 433/118 |
| 6,447,293 B1 | * | 9/2002 | Sokol et al. | 433/118 |

* cited by examiner

*Primary Examiner*—Cris L. Rodriguez
*Assistant Examiner*—Rachel Running

(57) ABSTRACT

In one embodiment of the present invention, an electric oral cleaning device is provided and includes a handle and a power supply contained therein. The device has a motor that drives a motor linkage, which includes a push rod that has one end that engages and moves a dental cleaning head about a center pin to cause an oscillation motion of the head. The entire head assembly is also interchangeable such that a flossing tool and various brushing tools may be utilized by the same device. In one aspect of the invention, the flossing tool includes a piece of slacked flossing material held between two arms defined by the flossing tool.

11 Claims, 16 Drawing Sheets

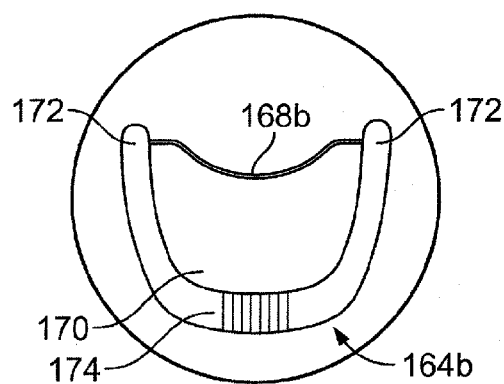
FIG. 5E
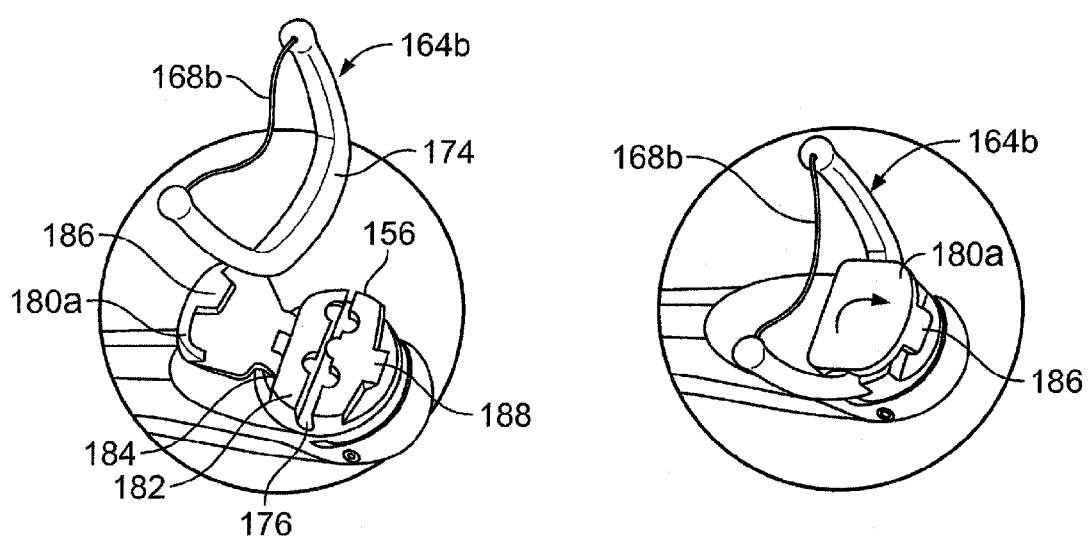
FIG. 5F
FIG. 5G

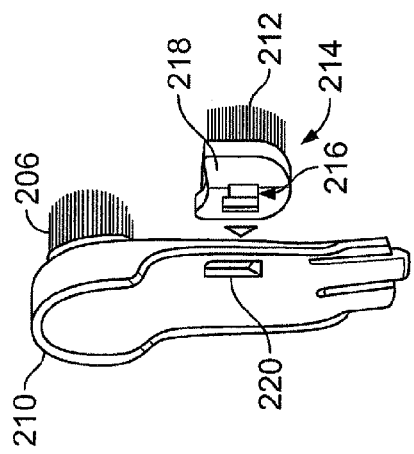
FIG. 6B
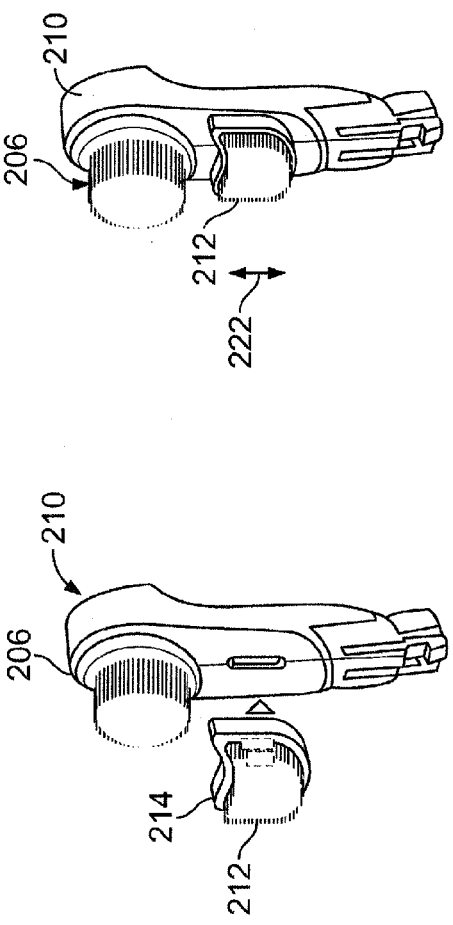
FIG. 6C
FIG. 6A
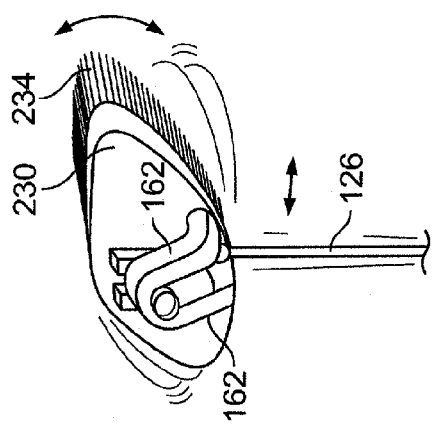
FIG. 7B
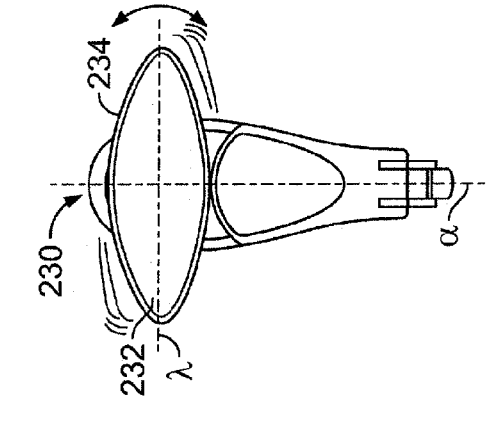
FIG. 7C
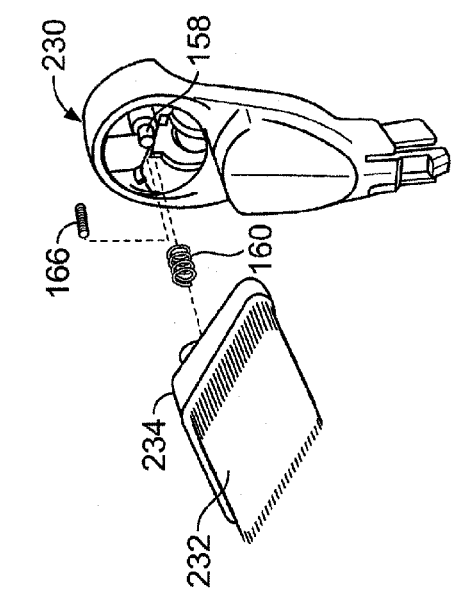
FIG. 7A

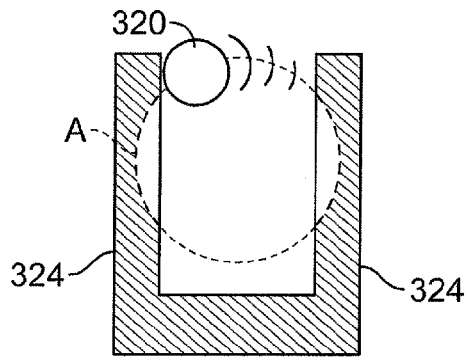 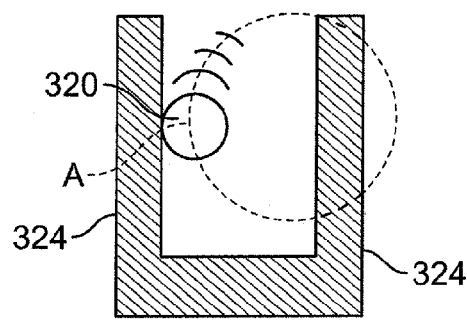
FIG. 10A              FIG. 10B
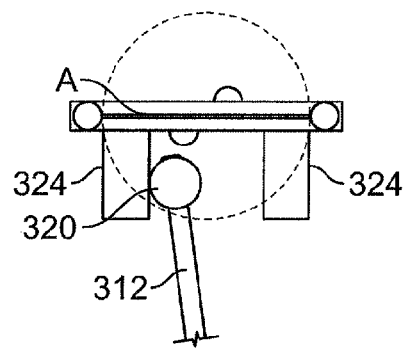 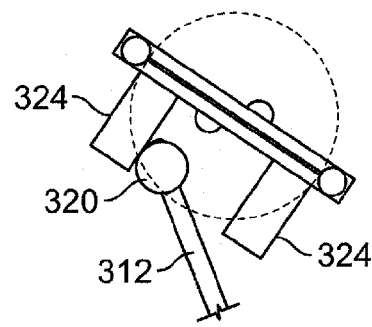
FIG. 11A              FIG. 11B
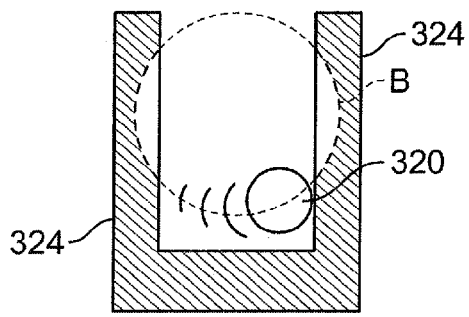 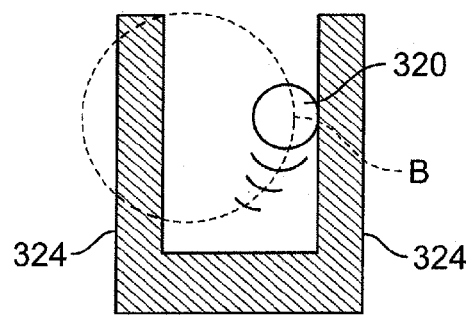
FIG. 10C              FIG. 10D
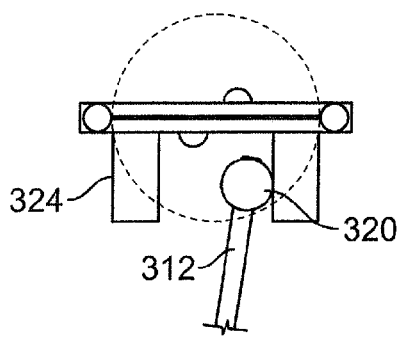 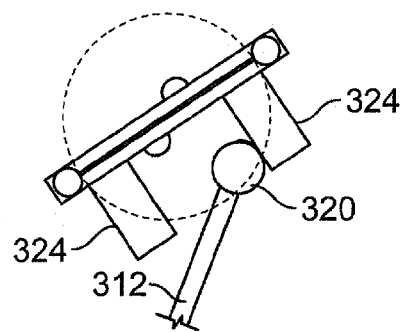
FIG. 11C              FIG. 11D

ELECTRIC ORAL CLEANING DEVICE

CROSS REFERENCE TO RELATED APPLICATIONS

This application is a continuation in part of U.S. Nonprovisional Application Ser. No. 10/886,235 filed Jul. 7, 2004, which claims benefit to U.S. Provisional Application Ser. No. 60/582,777, filed on Jun. 25, 2004.

FIELD OF THE INVENTION

The present invention relates to oral cleaning devices used to clean a user's mouth.

BACKGROUND OF THE INVENTION

Oral cleaning devices, both electric and non-electric, are known in the industry and in the prior art. Numerous patents have issued throughout the years to cover various improvements and novel features in the oral cleaning industry. Most oral cleaning devices directed to flossing require a sawing back and forth motion or a vibrating back and forth motion. For example, U.S. Pat. No. 5,170,809 requires a dental floss to be reciprocated along an axis substantially parallel to the axis of a handle (if the dental floss apparatus is positioned upright, the floss would be moving in an up and down motion). Alternatively, the motor mechanism moves a shaft in the handle only along the handle's longitudinal axis, which would impart the same movement in the dental floss attached to the shaft (again, the motion would be an up and down motion if the apparatus is standing in an upright position). U.S. Pat. RE 35,712 discloses a sonic dental device that includes a flossing head that stores extra dental floss such that a user may exchange used dental floss with new floss. U.S. Pat. No. 5,323,796 is directed to an automated dental flosser that includes a twine of floss held in the body of the device for which a user may dispense unused floss.

In one aspect of the prior art, movement of the oral cleaning heads (including flossing heads and brush heads) is done by vibrating the end of the neck of the device, such that the head vibrates or moves with the movement of the neck. In order to effectively transmit the vibration of the handle to the floss, the floss must be taut. Otherwise vibration is lost and no mechanical cleaning of the tooth by the electric flosser is achieved. The present invention provides for a different movement that may be beneficial to the user as it causes less lacerations and less sewing motion. The present invention also provides, in one embodiment, an electric oral cleaning device that includes interchangeable heads and provides for an oscillating head that may include a flossing tool or various brush head designs. In another aspect, the present invention provides for a loose piece of floss material secured between the two opposable arms of the flossing tool.

SUMMARY OF THE INVENTION

In accordance with an embodiment of the present invention, an electric oral cleaning device is provided that includes various interchangeable heads. In one aspect, the interchangeable head is a flossing head with a removable flossing tool, such that when used the flossing tool may be removed, discarded, and replaced with a new flossing tool. The electric oral cleaning device has a motor that drives a cam. Engaged to the cam is a carrier, which transposes rotational motion of the cam to a side-to-side motion. The carrier engages a rod that includes a fulcrum secured at a point along the length thereof. The other end of the rod is in communication with one of the interchangeable heads. The head includes a section that is moveably connected thereto. As the cam rotates, the second end of the rod moves in a side-to-side direction that pushes against walls secured on the moveable section of the head. As the rod contacts the walls, the moveable section oscillates counterclockwise and clockwise about a pin.

In another aspect of the invention, the interchangeable head includes a piece of floss material held between a pair of arms and the floss material that has a predetermined length such that there is slack in the floss material between the pair of arms.

In another aspect of the invention, the interchangeable head includes a locking cap that secures the removable flossing tool to the moveable head. The locking cap may further include a safety pad to reduce any pain from the user, accidentally bumping their teeth during cleaning.

In other aspects of the present invention, the interchangeable heads may include sections utilized to clean other parts of the user's mouth, such as but not limited to the teeth and tongue.

Numerous other advantages and features of the invention will become readily apparent from the following detailed description of the invention and the embodiments thereof and from the accompanying drawings.

BRIEF DESCRIPTION OF THE DRAWINGS

A fuller understanding of the foregoing may be had by reference to the accompanying drawings, wherein:

FIG. 5e is a front view of another flossing tool with a piece of slack flossing material held between two arms;

FIG. 5f is a perspective view of the flossing tool of FIG. 5e being attached to the flossing head;

FIG. 5g is a perspective view of the flossing tool of FIG. 5e with the retaining cap closed;

FIGS. 6a and 6b are front and back perspective views of another brush head assembly interchangeable with the head assemblies of the device of FIG. 1 and having oscillating bristles and non-oscillating but movable bristles;

FIG. 6c is a perspective view of the brush head assembly from FIG. 6a illustrating the movement of the non-oscillating but movable bristles;

FIGS. 7a and 7b are front and back perspective views of another brush head assembly with an oval oscillating brush head with the oval brush head being attached with its longitudinal axis being aligned perpendicular with axis of the brush head assembly;

FIG. 7c is a front view of the oval brush head assembly of FIG. 7a, illustrating the movement of the brush head;

FIG. 8b is a back perspective view of the flossing head assembly from FIG. 8a;

FIGS. 10a–10d are top views illustrating the movement of the second end of the rod of FIG. 9 and its contact with the walls that may be secured to a head;

FIGS. 11a–11d are side views corresponding to 10a–10d illustrating movement of the second end of the push rod and its effect on a flossing tool.

FIG. 12c is a back perspective view of the device from FIG. 12a showing the device with a sliding on/off switch along with the momentary switch illustrated in FIG. 12a;

FIG. 12e is an exploded view of the device from FIG. 12a; and

DETAILED DESCRIPTION OF THE EMBODIMENTS

Figure 1:
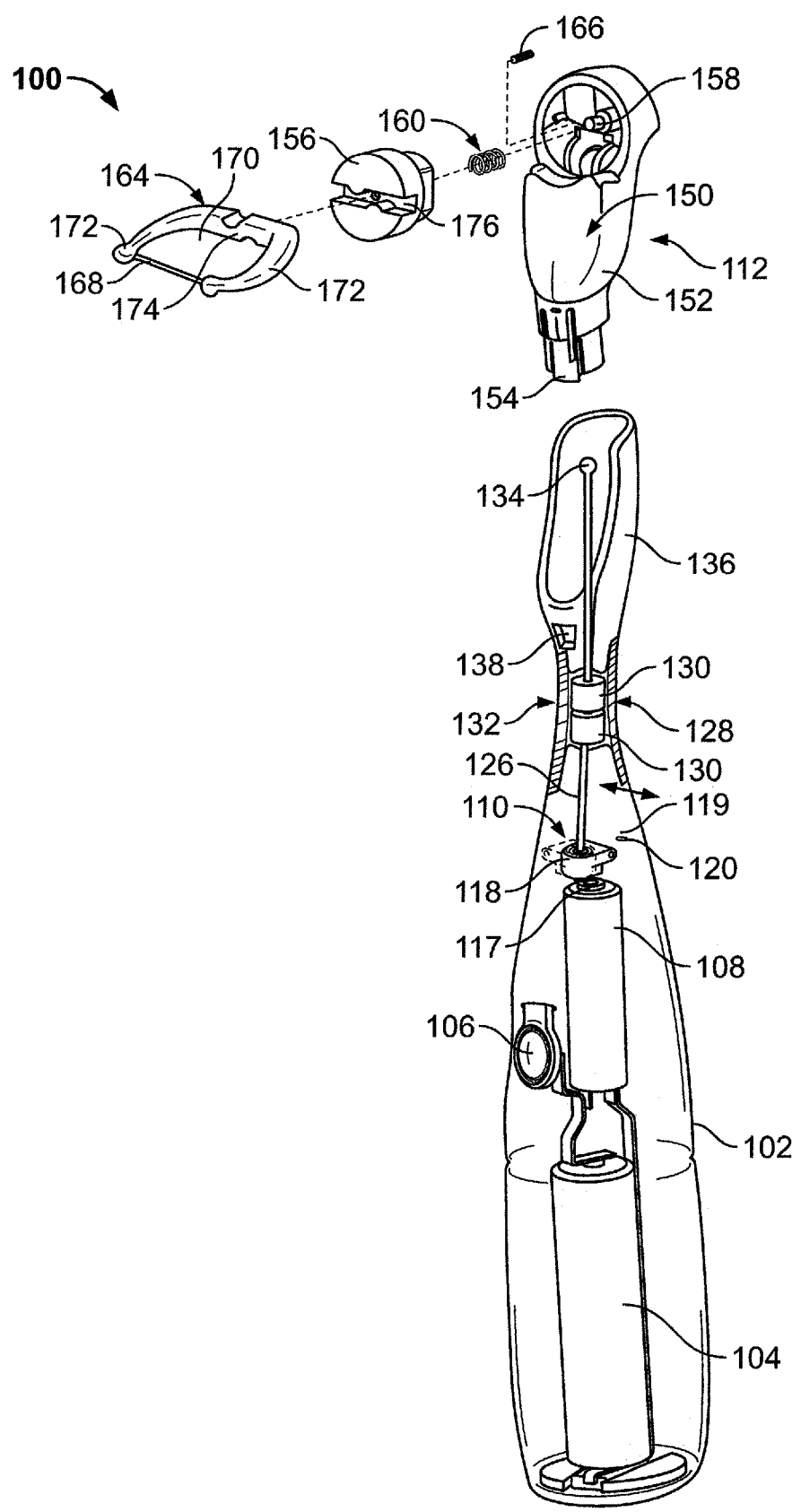
FIG. 1 is a partially exploded perspective view that also illustrates the internal components of a first electric oral cleaning device.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention to the embodiments illustrated.

Referring now to FIGS. 1 through 4 and in accordance to a first embodiment, an electric oral cleaning device is illustrated and generally referenced to as 100. The first device 100 includes a handle section 102 that a user grasps during use of the device 100. The handle section 102 houses a power supply 104 (such as a battery), which is in electrical communication with an activation button 106 and a motor 108. The motor 108 drives a linkage mechanism 110 that converts the rotational movement of the motor 108 to a back and forth ("oscillating") motion of a cleaning tool 112 (discussed in detail below).

Figure 2:
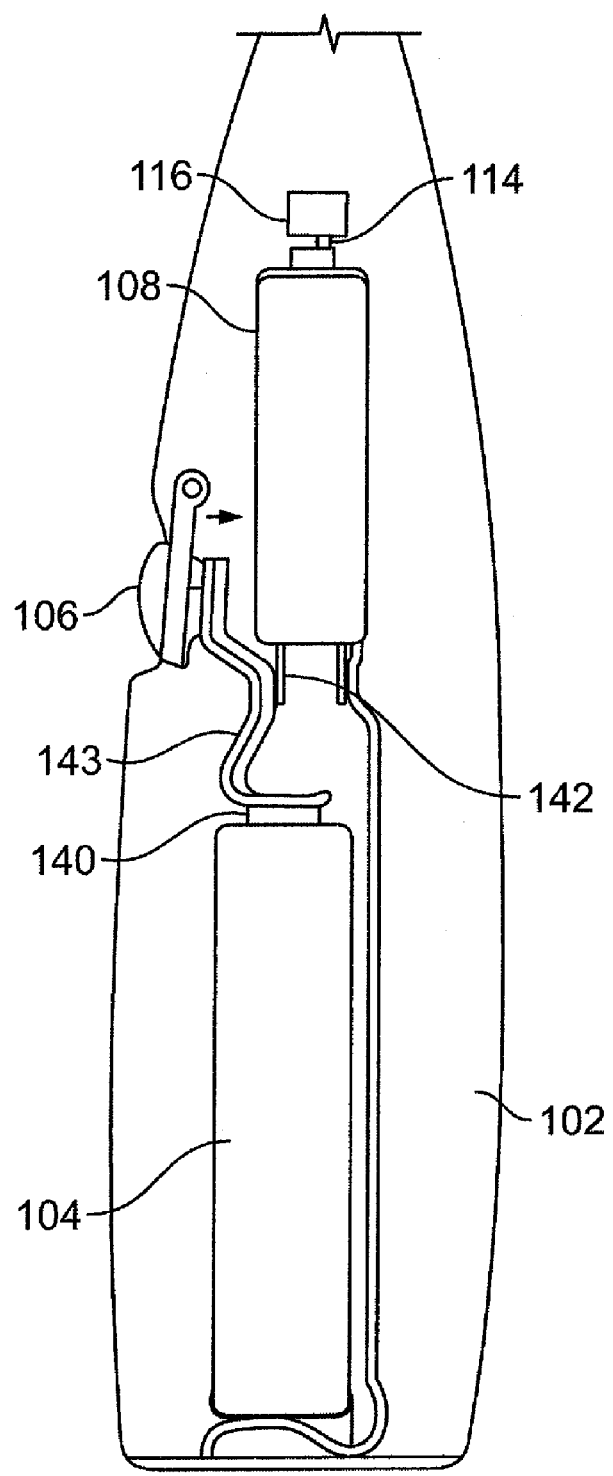
FIG. 2 is a side view of the activation button of the device illustrated in FIG. 1.
Figure 3:
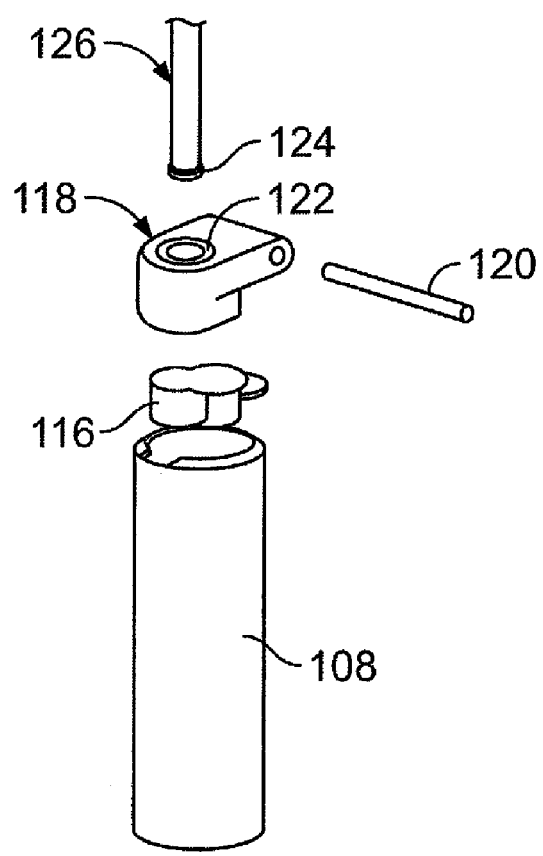
FIG. 3 is a perspective view of the motor mechanism and rotary to linear motion linkage utilized in the device of FIG. 1.
Figure 4:
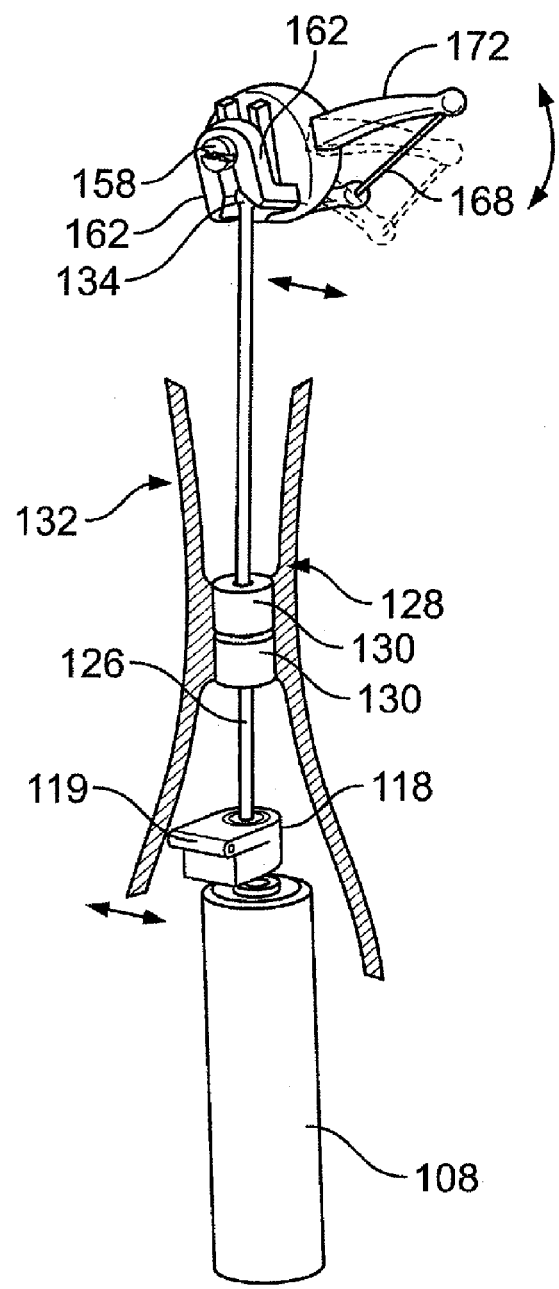
FIG. 4 is a perspective view of the motion linkage and a flossing head in the device of FIG. 1.

The linkage mechanism 110 includes a cam 116 secured to the drive shaft 114 of the motor 108 (FIG. 2). A carrier 118 is slidably attached on a pin 120 to the handle 102 (FIG. 3). The carrier includes apertures on the bottom portion (not shown) and on the top portion (aperture 122). The aperture on the bottom portion is sized such that the carrier 118 sits directly on the cam 116. The aperture 122 on the top portion of the carrier 118 is sized to receive a first end 124 of a rod 126. The linkage mechanism 110 further includes a fulcrum 128 secured along the length of the rod 126 (FIG. 4). Preferably, the fulcrum 128 is a pair of bushings 130. The rod 126 extends through a neck 132 of the device 100 and has a second end 134 that extends into a head support 136 (FIG. 1). As the cam 116 rotates (arrows 117), the carrier 118 slides side-to-side (arrows 119); as such the rotational motion is converted to a side-to-side motion. The side-to-side motion on the first end 124 of the rod 126 is moved along the length of the rod 126 through the fulcrum 128 to the second end 134. Thus, when the motor 108 is activated, the second end 134 of the rod 126 will move side-to-side.

As illustrated more closely in FIG. 2, activation of the motor 108 is achieved when the button 106 is pushed inwardly by the user. When the button 106 is pushed, the button 106 pushes a circuit contact 143, which is connected to a battery contact 140, towards a motor contact 142 such that an electrical circuit between the two contacts 140 and 142 is completed. The button 106 and/or the circuit contact 143 are normally biased outwardly (either by the use of a spring or resilient material [not shown]) such that when the button 106 is released the electrical circuit between the battery contact 140 and the motor contact 142 is broken causing the motor to automatically turn off. The device may have separate on/off buttons.

Continuing to refer to FIGS. 1 and 4, the head support 136 may be designed to receive removable head assemblies, such that various oral cleaning instruments may be employed, such as, but not limited to, various brushing head assemblies (described in detail below) and/or various flossing head assemblies. In addition the orientation of the flossing member may be angled in relation to the handle or parallel to the handle.

In one aspect of the present invention, the head support 136 receives a removable flossing head assembly 150 (FIG. 1). The flossing head assembly 150 includes a flossing head housing 152 with a locking flange 154 that slides into engagement with an aperture 138 on the head support 136. To disengage the flossing head assembly 150, the user presses the locking flange 154 while pulling the flossing head assembly 150 away from the head support 136.

The flossing head assembly 150 further includes a flossing head 156 that is rotatably secured about a pin 158 on the flossing head housing 152. A tension spring 160 may be placed between the flossing head 156 and the flossing head housing 152. Engaged or secured to the flossing head 156 are walls 162 (FIG. 4). The second end 134 of the rod 126 is placed between the walls 162 in order to assist in transposing the side-to-side motion of the second end 134 of the rod 126 into a counterclockwise and clockwise oscillating motion of the flossing head 156. As the second end 134 of the rod 126 moves side-to-side, the second end 134 alternately contacts and pushes the walls 162 outwardly from its center axis of rotation (the pin 158). The force against the walls 162 will cause the flossing head 156 to oscillate about the pin 158. The oscillating motion will cause a flossing tool 164 attached to the flossing head 156 to oscillate counterclockwise and clockwise. The flossing head 156 is retained in the flossing head housing by one or more retainer pins 166.

As seen in FIG. 1, the flossing tool 164 has a section of flossing material 168 suspended over a cavity 170 that is created between two opposable arms 172, which extend from a support region 174. The support region 174 frictionally fits into a channel 176 on the flossing head 156, thereby permitting a used flossing tool 164 to be replaceable.

The flossing head 156 is also secured perpendicularly to the device 100 such that the flossing tool 164 extends perpendicularly away from the device 100. However, the flossing head or flossing tool 164 may be secured at various angles offset from the axis of the device 100.

Figure 5A:
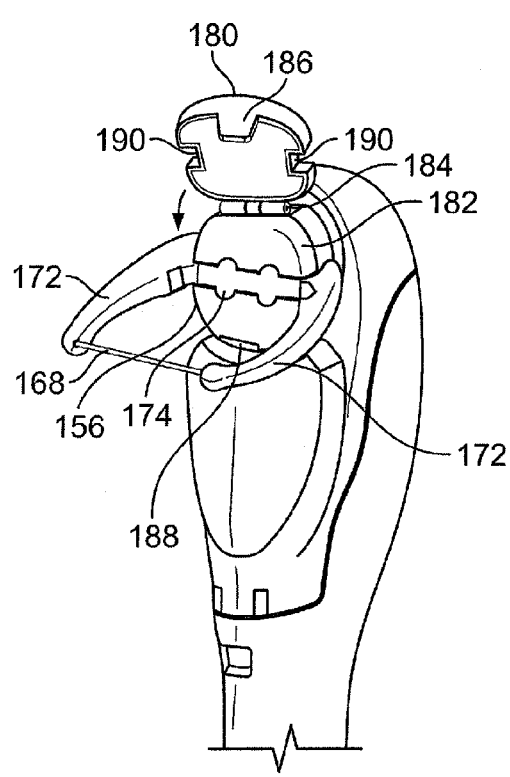
FIG. 5a is a perspective view of another flossing head with an opened locking cap.
Figure 5B:
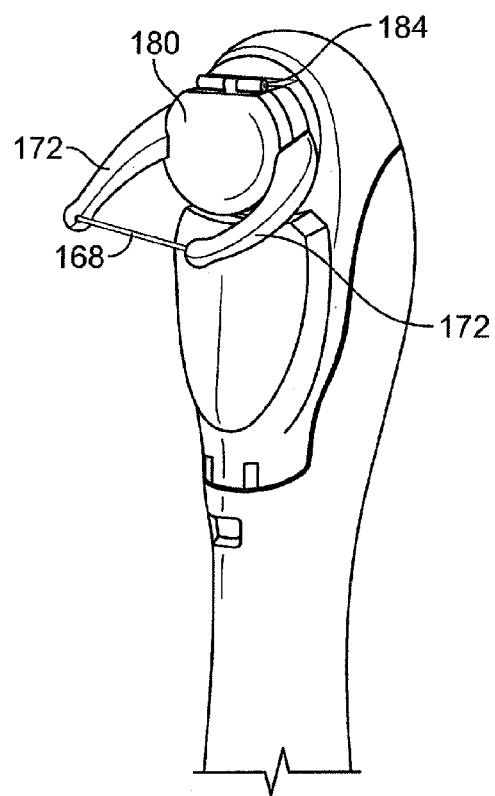
FIG. 5b is a perspective view of the flossing head of FIG. 5a with the locking cap closed.

In another aspect of the present invention, the flossing head 156 may include a locking cap 180, illustrated in FIGS. 5a and 5b. The locking cap 180 is hinged 184 on one side to the face 182 of the flossing head 156. The locking cap 180 would also include a tab 186 that frictionally fits into a corresponding detent 188 on the face 182 of the flossing head 156. The locking cap 180 prevents the flossing tool 164 from separating from the flossing head 156. In addition, the locking cap 180 also includes side grooves 190 that receive the opposing arms 172 of flossing tool 164 and presses the arms 172 outwardly from each other to maintain a taut flossing material 168.

Figure 5C:
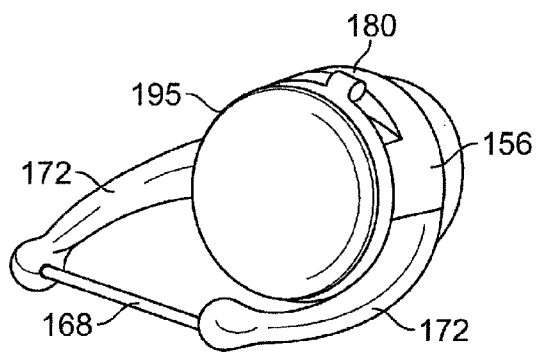
FIG. 5c is a perspective view of another flossing head showing a locking cap with a soft pad placed thereon.
Figure 5D:
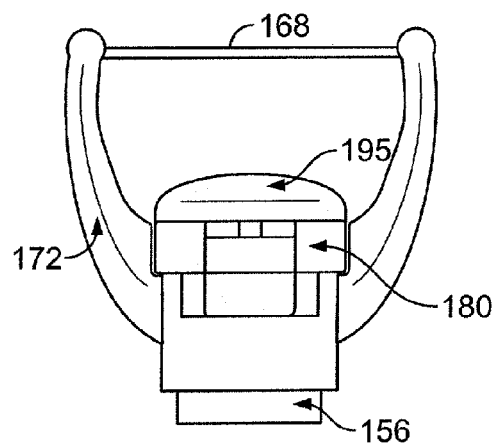
FIG. 5d is a side view of the flossing head from FIG. 5c.

Referring now to FIGS. 5c and 5d, the locking cap 180 includes a pad 195 made of soft rubber or a soft PVC material. If the flossing member slides between the teeth abruptly the locking cap 180 can bump into the teeth. The safety pad 195 helps provide a cushion between the locking cap 180 and the user's teeth (FIG. 5b). The safety pad 195 may be rotational independent from the cap acting as a governor to prevent deep action.

In another aspect of the present invention, a flossing tool 164b has a section of flossing material 168b that has a predetermined length such that there is slack in the flossing material, shown in FIG. 5e. The slacked flossing material will maintain a center bowing portion. In addition, the predetermined length of the slacked flossing material is not too long such that the flossing material bows all the way down to the support region 174. It is important that the slacked flossing material is such that the user will still have an adequate cleaning of their teeth. The slack is dangled over the cavity 170 that is created between the two opposable arms 172 that extend from a support region 174 and which secure the ends of the flossing material 168b. As mentioned in reference to the other flossing tool, in this aspect of the present invention, the flossing tool 164b may be secured to the flossing head 156 by frictionally fitting the support region 174 into a channel 176 on the flossing head 156. To lock the flossing tool 164b to the flossing head 156, a locking cap 180a is moved from an open position, FIG. 5f, to a closed position, FIG. 5g. In this embodiment the locking cap 180a does not engage the two opposable arms 172 such that the flossing material is pulled to a taut position, meaning that even when the locking cap 180a is closed, the flossing material will continue to be slacked.

Figure 5H:
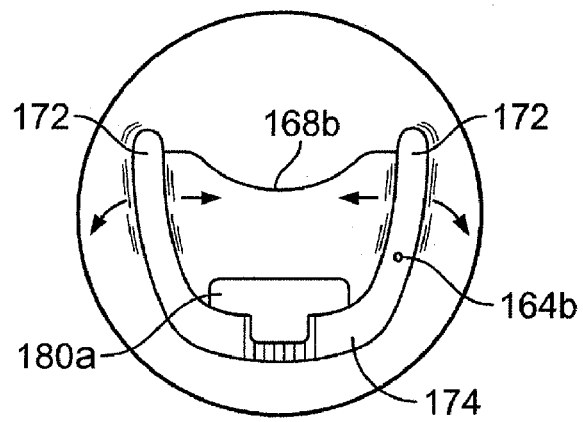
FIG. 5h is a front view of the flossing tool of FIG. 5e illustrating the relative movement of the flossing tool arms during operating.
Figure 5I:
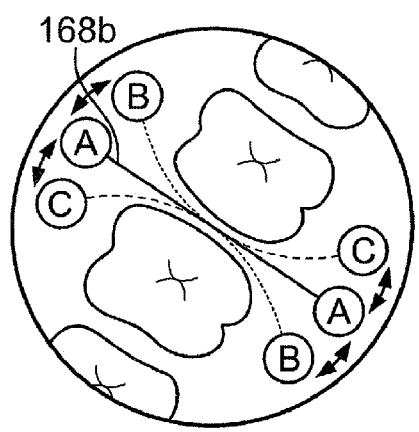
FIG. 5i is a top view of the relative movement of the flossing material from FIG. 5e between two teeth.
Figure 5J:
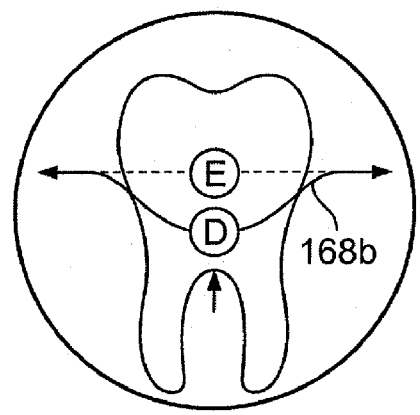
FIG. 5j is a front view of the relative movement of the flossing material from FIG. 5e against a tooth.

Referring now to FIG. 5h to FIG. 5j, during operation with a slacked flossing material 168b, the flossing tool 164b will oscillate in a back and forth motion as discussed above. The flossing material 168b will travel in a curved and arced motion to and from position B (FIG. 5i) and position C (FIG. 5j). Having a slacked flossing material helps to increase the area of the tooth that is being cleaned. Moreover, the flossing tool 164b may include flexible arms 172. Flexible arms 172 with a slacked flossing material provides for a unique cleaning action. When the flossing tool 164b oscillates, the flexible arms move between positions A, B, and C (FIG. i), as the flossing tool moves to position B and C the slacked flossing material will move to a tauter position, from position D to E (FIG. j). This is because the distance between the arms in position B and C is longer as the flossing tool oscillates about a tooth. This increases the area of the tooth that will be cleaned, as the flossing material moves from position D (slack position) to position E (taut position). The flexible arms also aids in preventing injury to a user if the same comes into contact with a portion of the user mouth or tooth; the flexible arm will bend or move around the point of contact rather then a rigid arm that would push against the point of contact.

In another aspect of the present invention illustrated in FIG. 6a through 6c, a brush head assembly 210 may employ oscillating bristles 206 movably controlled by the motor described herein above. The brush head assembly 210 also includes nonoscillating but movable bristles 212. The non-oscillating but movable bristles 212 are secured to a secondary brush head 214 that includes a protrusion 216 on the backside 218 thereof. The protrusion 216 fits into a slot 220 positioned on the brush head assembly 210 that permits the secondary brush head 214 to freely slide within the slot 220. During use, the secondary brush head 214 will move along the slot 220 towards and away from the oscillating bristles 206 (illustrated by arrows 222 in FIG. 6c) when the user presses the secondary brush head 214 onto its teeth and moves the device 100.

In yet another aspect of the invention (FIGS. 7a through 7c), a brush head assembly 230 may include oscillating bristles 232 attached to an oval brush head 234. The oval brush head 234 is secured to the brush head assembly 230 similarly to that which has been previously described. In addition the oval brush head 234 is orientated such that the longitudinal axis X (its long axis) is aligned to be perpendicular to the axis (referenced as a in FIG. 7c) of the brush head assembly 230. As such, the orientation and oscillation of the oval brush head 234 would allow for a good cleaning of the user's tongue.

Figure 8B:
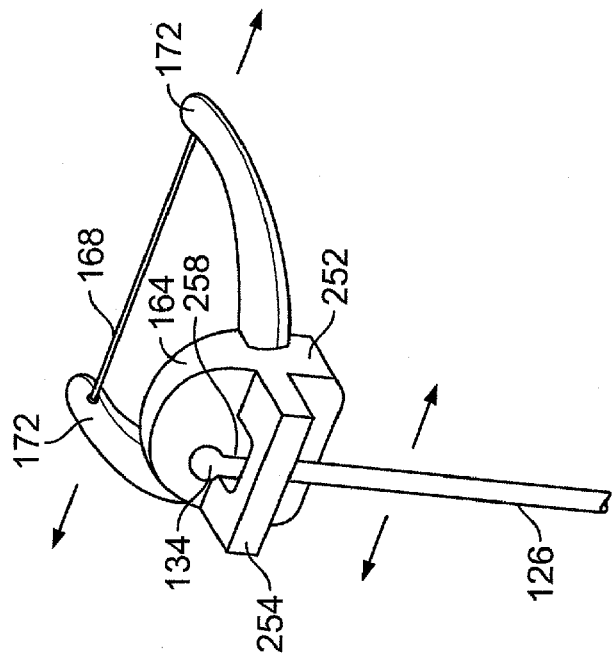
Figure 8A:
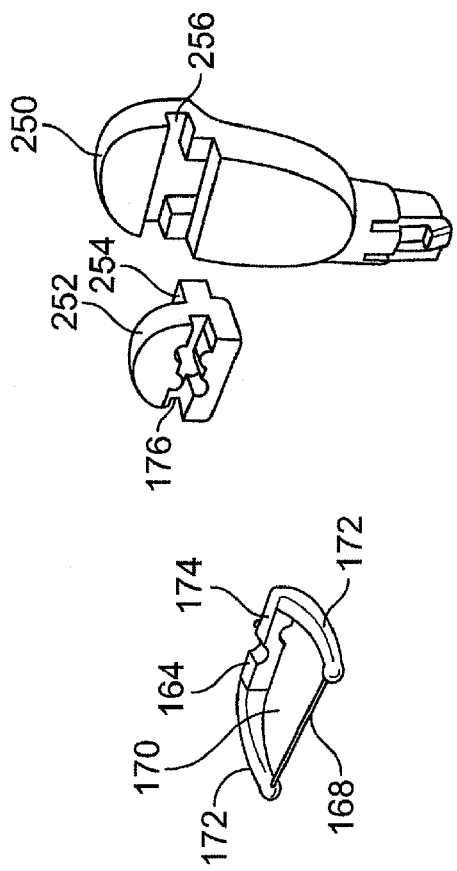
FIG. 8a is a front perspective view of another flossing head assembly with a side-to-side movement of the flossing tool.
Figure 8C:
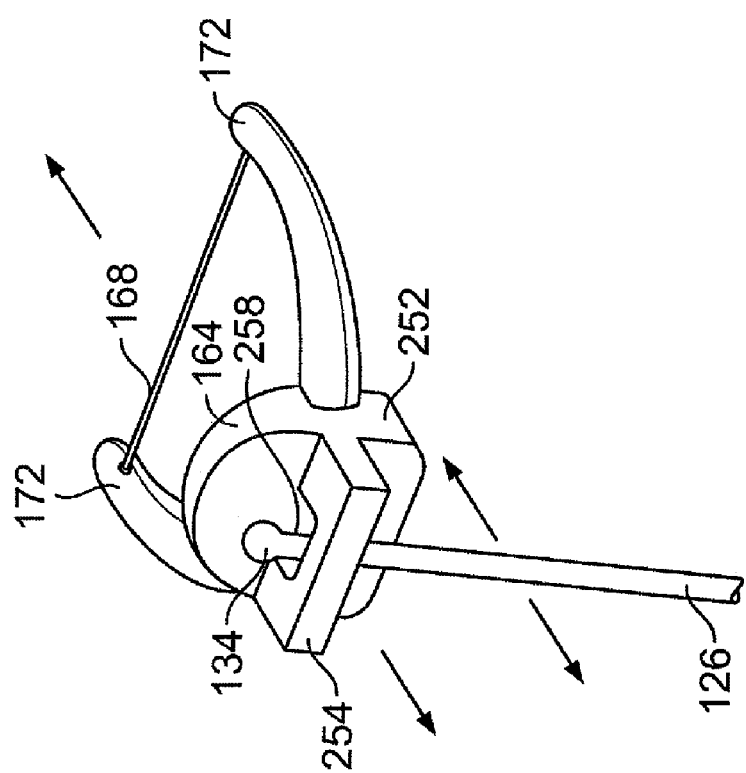
FIG. 8c is a back perspective view of the flossing head assembly from FIG. 8a, where the movement of the flossing head is in a back and forth sawing motion.

In yet another aspect of the invention (FIGS. 8a and 8b) a flossing head assembly 250 may include side-to-side motion, rather than the rotational oscillating motion. The flossing head assembly 250 includes a moveable section 252, which has a bracket 254 on the backside thereof. The bracket 254 slides within a groove 256 defined by the flossing head assembly 250. A disposable flossing tool 164 is in removable engagement with the moveable section 252, as previously described. As shown in FIG. 8b, the second end 134 of the rod 126 is inserted into an opening 258 defined by the bracket 254 on the backside 254 of the moveable section 252. When the second end 134 is moving in the side-to-side motion, the moveable section 252 will also move in a back and forth or side-to-side motion, causing the same movement in the flossing tool 164. Moreover, the moveable section 252 will also be secured within the groove 256 by virtue of the second end 134 being inserted into the bracket 254; as movement of the moveable section will be limited to the movement of the second end. Referring now to FIG. 8c, the flossing head assembly 250 may be controlled to move in a back-to-forth sawing motion. The sawing motion or movement of the rod 126 is perpendicular to the alignment of the flossing material 168.

Figure 9:
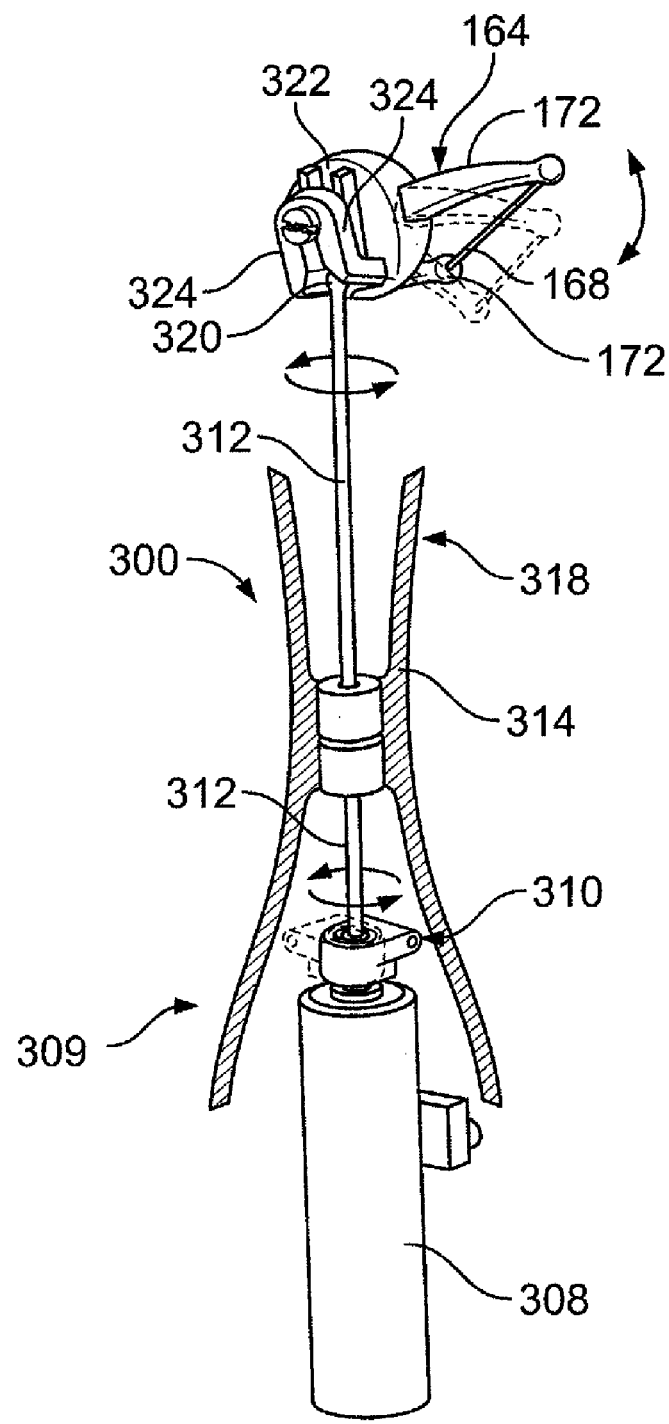
FIG. 9 is a perspective view of a motion linkage in accordance with a second embodiment of the present invention and illustrating a flossing head.

Referring now to FIG. 9, in a second embodiment, an electric oral cleaning device is illustrated and generally referenced to as 300. The device 300 is similar to the first embodiment 100 except that the motor 308 drives a differently configured linkage mechanism 309. In the second embodiment device 300, the motor 308 drives a cam 310 that has secured thereto at an offset position the first end of a rod 312. Secured along the length of the rod is a fulcrum 314. The rod 312 extends through a neck 318 of the device 300 and has a second end 320 that extends into the head support (as illustrated in FIG. 1). This configuration tends to transpose the rotational motion of the motor 308 to a circular motion in the second end 320 of the rod 312.

Referring now to FIGS. 10a through 10d and corresponding FIGS. 11a through 11d, as the second end 320 of the rod 312 moves in a circular direction and as the second end 320 approaches point A on its circular motion (FIGS. 10a and 11a) it contacts walls 324 secured to the flossing head 156 (or other head attached thereto). Once the second end 320 contacts one of the walls 324, the flossing head 156 will move about the pin 158 in the direction the second end 320 is traveling (FIGS. 10b and 11b). This causes one of the flossing arms 172 to be in a higher position then the other arm. Similarly, as the second end 320 continues to move to the opposite point B on its circular motion (FIGS. 10c and 11c), the second end 320 contacts the walls 324 causing the flossing head 156 to move in an opposite direction, (FIGS. 10d and 11d). The back and forth oscillating motion of the flossing head 156 acts to move the flossing tool 164 (and thus the flossing material 168) in a fluttering like motion.

Figure 12A:
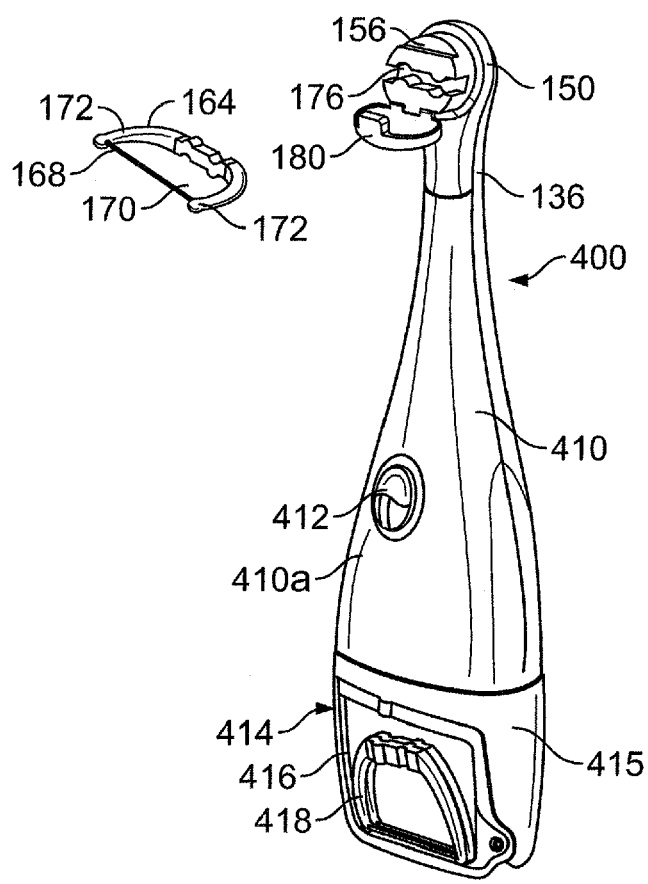
FIG. 12a is a front perspective view of another embodiment of the present invention showing a device with a spare flosser compartment.
Figure 12B:
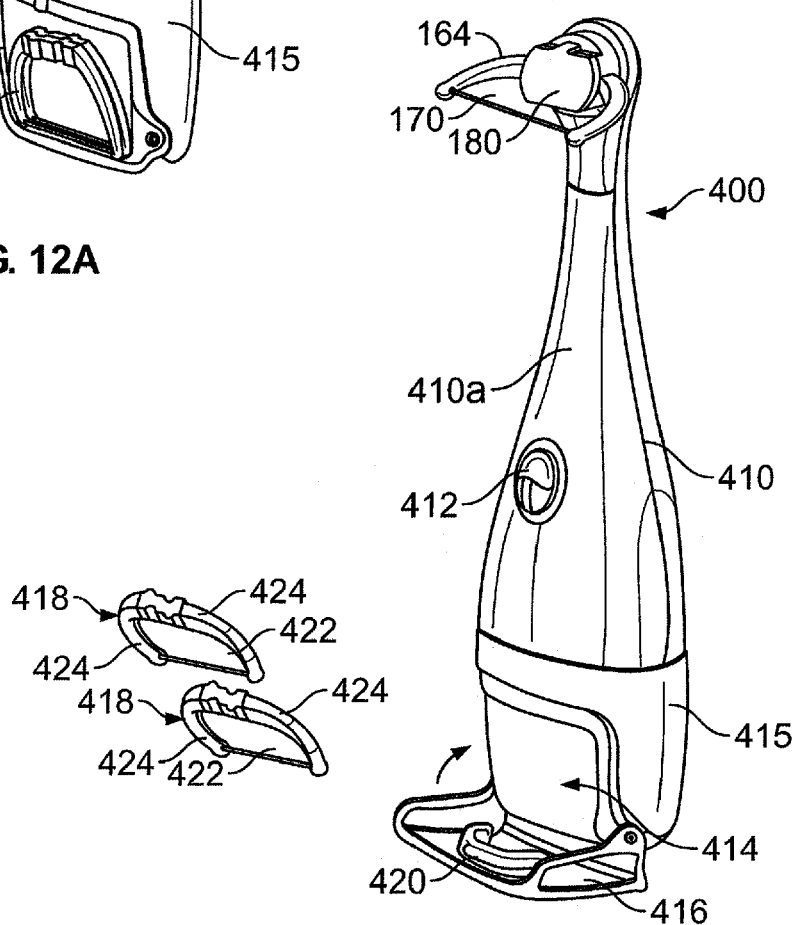
FIG. 12b is a front perspective view of the device from FIG. 12a with the spare compartment door opened.

Referring now to FIGS. 12a and 12b, in another embodiment of the present invention, an electric oral cleaning device is illustrated and generally referenced to as 400. The electric oral cleaning device includes a replaceable flossing tool 164 (as described above) that frictionally fits into a groove 176 defined on the flossing head 156. In this particular embodiment, the flossing head assembly 150 is not removable from the head support 136. However, the flossing head 156 will still oscillate in a counterclockwise and clockwise motion, as mentioned above. In addition, the flossing head 156 includes a locking cap 180.

The device 400 further includes a momentary switch 412 positioned through the front casing 410a of the hand-held body 410, which when a user presses inwardly, the momentary switch 412 will activate the oscillation of the flossing head 156. As soon as the user releases the momentary switch 412 the oscillation will cease as power to the device 400 is no longer provided.

The body 410 of the device 400 includes a spare flosser tool compartment 414 in a lower portion 415 of the body 410. The spare flosser compartment 414 is accessible through a compartment door 416. In this embodiment, the spare flosser tools 418 are placed on a member 420 projecting from the inside of the compartment door 416. The projecting member 420 receives the cavity 422 defined between the flossing arms 424 on the spare flosser tools 418 and holds the spare flosser tools 418 by frictionally engaging the flossing arms 422 (see FIG. 12b). However, the spare flosser tools 418 may in another embodiment simply be stored loosely in the spare flosser compartment 414. This provides for an easy compact electric travel device.

Figure 12C:
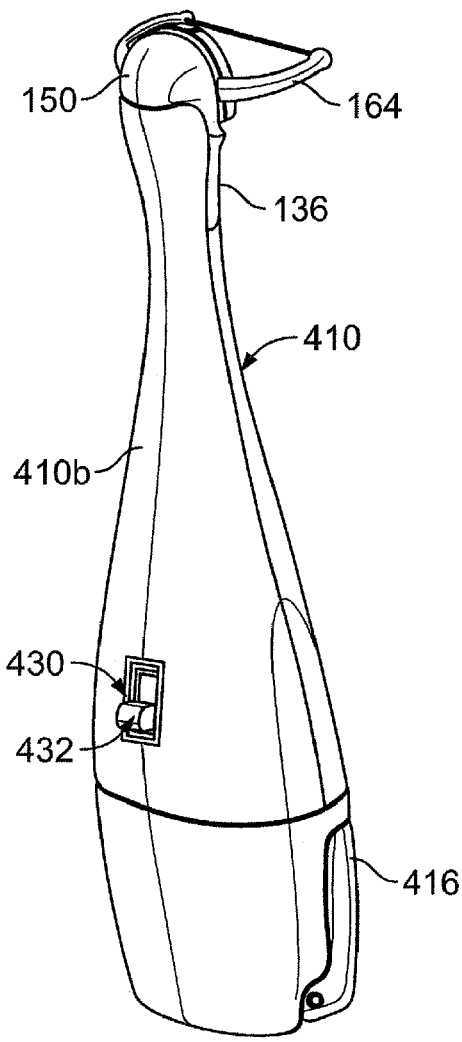

Referring now to FIG. 12c the device 400 also includes an activation switch 430 extending out of the back casing 410b of the hand-held body 410. The activation switch 430 has an off position and an on position. The switch 430 slides between the two positions. When moved to the on position, the activation switch 430 activates the device such that use of the momentary switch is not necessary. When the activation switch 430 is in the on position, the device 400 may only be turned off by sliding the activation switch 430 to its off position. This provides the user with two types of activation buttons, the momentary button 412 and the activation switch 430. This also may be useful in packaging, as access to the momentary button 412 through the packaging may be provided, allowing a potential consumer to view the operation of the device without having to also turn the device off. This prevents the potential consumer from leaving the device on and draining the power supply before the device is purchased.

Figure 12D:
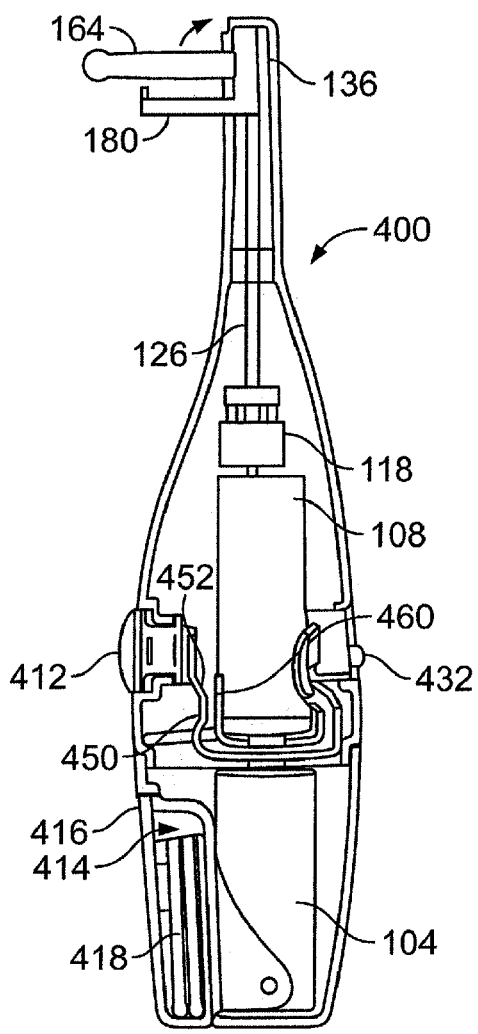
FIG. 12d is a side view of the device from FIG. 12a showing the internal electrical components.
Figure 12E:
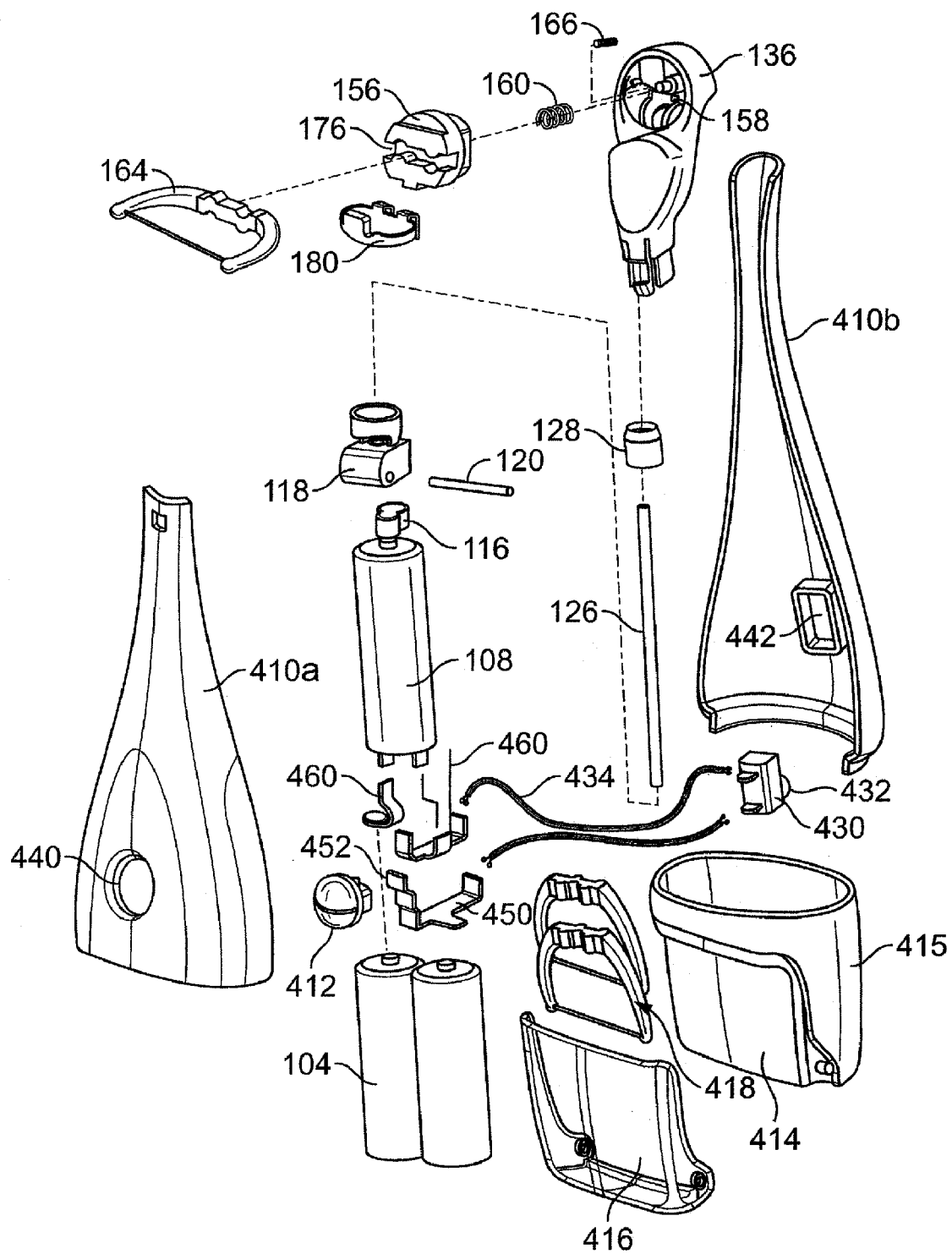

Turning now to FIGS. 12d and 12e, the internal components along with the activation of the device is discussed in further detail. Like components from previous embodiments are referenced by similar numerals. The control of the oscillating flossing tool 164 is similar to the previous embodiments and thus is not discussed in reference to this device. However, unlike the previous embodiments, the current device 400 includes two activation buttons. The momentary button 412 extends through an opening 440 on the front casing 410a of the body 410. The momentary button 412 is positioned against a first battery contact 450 that is connected to the power supply 104. When pressed inwardly, the momentary button 412 pushes a resilient rod 452 defined by the first battery contact 450 such that the resilient rod 452 makes contact with a motor contact 460, which leads to activation of the motor 108. When released, the resilient rod 442 releases its contact with the motor contact 460 turning off the motor 108.

The activation switch 430 extends through an aperture 442 in the back casing 410b of the body 410. The activation switch 430 is electrically connected through wires 434 to the battery contact 450 and the motor contact 460. The activation switch 430 includes a sliding knob 432 that when moved to the on position, will close the circuit between the battery contact 450 and the motor contact 460 such that the motor 108 is activated. When the knob 432 is moved or is in the off position, the circuit is broken and the motor 108 is turned off.

Figure 12F:
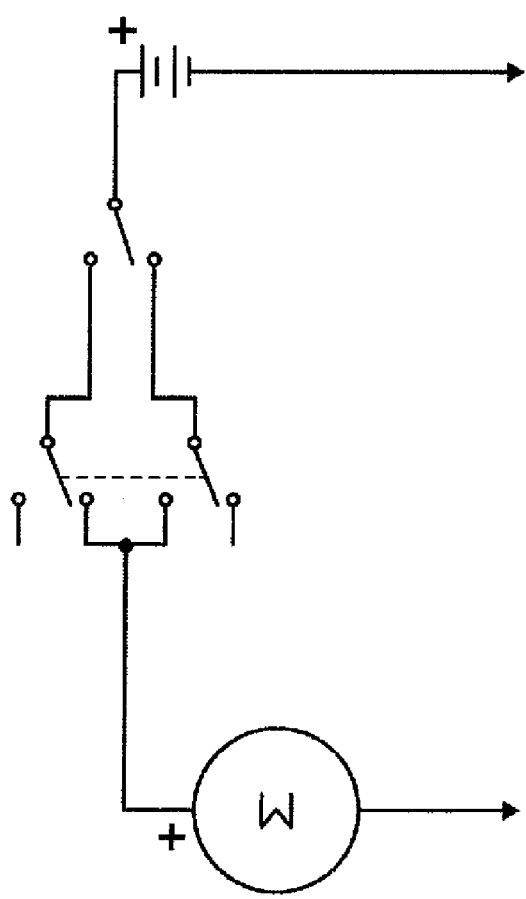
FIG. 12f is an electrical schematic showing a dual switch device with a momentary switch that changes the activation of the device set by the second switch.

In another aspect of the invention and as illustrated in FIG. 12f, the back side sliding knob 432 may be a polarity switch working in concert with the front momentary button 412. When the sliding knob 432 is in a first position, the device is on with the momentary button 412 acting to momentary turn the device off only when the button 412 is held in by the user. When the sliding knob 432 is in a second position, the device is turned off with the momentary button acting to momentary turn the device on only when the button 412 is held in by the user.

From the foregoing and as mentioned above, it will be observed that numerous variations and modifications may be effected without departing from the spirit and scope of the novel concept of the invention. It is to be understood that no limitation with respect to the specific embodiments illustrated herein is intended or should be inferred.

I claim:

1. An electric flosser comprising:
a body having a handle portion and a head portion, the head portion including a movable section rotatably connected thereto;
an electrically operated motor in said handle portion;
a means interconnecting said motor and said movable section to oscillate said movable section in a clockwise and counterclockwise direction;
a channel defined on said movable section;
a flossing tool having a section in removable engagement with said channel, the flossing tool having a piece of slacked flossing material held between two arms defined by said flossing tool, said slacked flossing material has a length defined to create a bowed portion between said two, arms and;
a cap hinged to said movable section, said cap and said movable section include a means to secure the cap in a closed position over said channel when the section of said flossing tool is in engagement with said channel, wherein said closed position prevents the flossing tool from separating from said movable section, whereby when said motor is operated the flossing tool is oscillated in a clockwise and counterclockwise direction.

2. The electric flosser of claim 1, wherein the head portion includes a locking flange and the body includes a notch that receives said locking flange to place the head portion in removable engagement with the body.

3. The electric flosser of claim 1, wherein the cap includes a pad on an outside portion defined by the cap, such that the pad is positioned within the cavity of the flossing tool when the cap is in the closed position.

4. The electric flosser of claim 1, wherein the two arms of the flossing tool are flexible such that during oscillation of the flexibility of the arm tends to pull the slacked flossing material to a taut position.

5. An electric flosser comprising:

a body having a handle portion and a head portion, the head portion including a movable section connected thereto;

an electrically operated motor in said handle portion;

a means interconnecting said motor and said movable section to move said movable section; and the movable section including a flossing tool that has a piece of slacked flossing material held between two arms defined by said flossing tool, said slacked flossing material has a length defined to create a bowed portion between said two arms, and wherein the movable section includes a channel and the flossing tool has a section in removable engagement with said channel such that the flossing tool is replaceable; and a cap hinged to said movable section, said cap and said movable section include a means to secure the cap in a closed position over said channel when the section of said flossing tool is in frictional engagement with the channel, wherein said closed position prevents the flossing tool from separating from said movable section, and the cap being hinged to said movable section such that an outside portion defined by said cap faces the flossing material when said flossing tool is in engagement with the channel, whereby when said motor is operated the flossing tool is moved.

6. The electric flosser of claim 5, wherein the two arms are flexible.

7. The electric flosser of claim 5, wherein the cap includes a pad on an outside position defined by the cap such that the pad is positioned within the cavity of the flossing tool when the cap is in the closed position.

8. The electric flosser of claim 5 further comprising a lower portion defined by the body as being at an end along said handle and distal to said head portion, the lower portion having a means to store at least one flossing tool.

9. The improvement of claim 8, wherein the storing means is further defined by having a section of the lower portion being recessed to create a recessed compartment to accommodate at least one flossing tool and door movably attached to the recessed compartment.

10. The electric flosser of claim 5 further comprising:

a button positioned through a front casing defined by the body, the button operative by the user to connect the motor to a power source while the button is pushed inwardly, and a switch positioned through a back casing defined by the body, the switch having first and second positions, the switch when moved to the first position by the user connects the motor to the power source, and the switch when moved to the second position by the user disconnects the motor to the power source.

11. An electric flosser comprising:

a body having a handle portion and a head portion, the head portion including a movable section connected thereto;

an electrically operated motor in said handle portion;

a means interconnecting said motor and said movable section to move said movable section;

the movable section including a flossing tool that has a piece of slacked flossing material held between two arms defined by said flossing tool, said slacked flossing material has a length defined to create a bowed portion between said two arms, whereby when said motor is operated the flossing tool is moved a lower portion defined by the body as being at an end along said handle and distal to said head portion, the lower portion having a section being recessed to create a recessed compartment to accommodate at least one flossing tool and a door movably attached to the recessed compartment, wherein the door includes a projecting member that is sized to frictionally engage the opposable arms defined by the flossing tool, wherein a flossing tool in engagement with the projecting member is secured to the door.

\* \* \* \* \*